United States Patent
Wojciechowski et al.

(10) Patent No.: US 11,661,436 B2
(45) Date of Patent: May 30, 2023

(54) METHOD FOR PREPARING 3'-O-AMINO-2'-DEOXYRIBONUCLEOSIDE-5'-TRIPHOSPHATES

(71) Applicant: DNA Script SAS, Le Kremlin-Bicêtre (FR)

(72) Inventors: Filip Wojciechowski, Le Kremlin-Bicêtre (FR); Thomas Ybert, Paris (FR)

(73) Assignee: DNA SCRIPT SAS, Le Kremlin-Bicêtre (FR)

( * ) Notice: Subject to any disclaimer, the term of this patent is extended or adjusted under 35 U.S.C. 154(b) by 39 days.

(21) Appl. No.: 17/214,245

(22) Filed: Mar. 26, 2021

(65) Prior Publication Data

US 2021/0300961 A1   Sep. 30, 2021

(30) Foreign Application Priority Data

Mar. 30, 2020   (EP) ..................................... 20166719

(51) Int. Cl.
*C07H 19/20* (2006.01)
*C07H 1/04* (2006.01)
*C07H 19/10* (2006.01)

(52) U.S. Cl.
CPC ............... *C07H 19/20* (2013.01); *C07H 1/04* (2013.01); *C07H 19/10* (2013.01)

(58) Field of Classification Search
None
See application file for complete search history.

(56) References Cited

U.S. PATENT DOCUMENTS

| | | | |
|---|---|---|---|
| 7,544,794 B1 | 6/2009 | Benner | |
| 8,034,923 B1 | 10/2011 | Benner et al. | |
| 8,212,020 B2 * | 7/2012 | Benner | C07H 19/173 536/25.31 |
| 10,472,383 B2 | 11/2019 | Benner | |
| 11,180,520 B2 * | 11/2021 | Malyshev | C07H 19/10 |

FOREIGN PATENT DOCUMENTS

| | | |
|---|---|---|
| EP | 0381335 | 8/1990 |
| WO | 2020/043846 A1 | 3/2020 |

OTHER PUBLICATIONS

Jensen et al, "Template-independent enzymatic oligonucleotide synthesis (TiEOS): Its history, prospects, and challenges," Biochemistry, 57: 1821-1832 (2018).
Swamy et al., "Mitsunobu and Related Reactions: Advances and Applications," Chem. Rev., 109(6):2551-2651 (2009).
Kondo et al., "Synthesis of 5'(3')-O-amino nucleosides," Nucleic Acids Symp Ser., 16:93-96 (1985).
Burgess et al., "Synthesis of an oxyamide linked nucleotide dimer and incorporation into antisense oligonucleotide sequences," J. Chem. Soc. Chem. Comm., 8: 915-916 (1994).
Hutter et al. "Labeled nucleoside triphosphates with reversibly terminating aminoalkoxyl groups," Nucleosides, Nucleotides & Nucleic Acids, 29(11), 18 pages (2010).

* cited by examiner

*Primary Examiner* — Traviss C McIntosh, III
(74) *Attorney, Agent, or Firm* — Gardella Grace P.A.

(57) ABSTRACT

Methods for preparing 3'-O-amino-2'-deoxyribonucleoside-5'-triphosphates with reduced 3'-hydroxy-2'-deoxyribonucleoside-5'-triphosphate contamination by converting 3'-(N-acetone-oxime)-2'-deoxynucleoside triphosphate to 3'-O-amine-2'-deoxynucleoside triphosphate by treatment with an aryl-oxyamine and compositions produced therefrom.

8 Claims, 5 Drawing Sheets

RP-Nova-Pak-long-shorter fw -g after deprotection 001 and

METHOD FOR PREPARING 3'-O-AMINO-2'-DEOXYRIBONUCLEOSIDE-5'-TRIPHOSPHATES

RELATED APPLICATIONS

This application claims priority to European Patent Application No. EP20166719.3, entitled "Method for Preparing 3'-O-Amino-2'-Deoxyribonucleoside-5'-Triphosphates," filed Mar. 30, 2020. The above identified application is hereby incorporated by reference in its entirety.

BACKGROUND

Interest in enzymatic approaches to polynucleotide synthesis has recently increased not only because of increased demand for synthetic polynucleotides in many areas, such as synthetic biology, gene modification, high-throughput sequencing and molecular diagnostics, but also because of the limitations of chemical approaches to polynucleotide synthesis, such as upper limits on product length and the use and needed disposal of organic solvents, Jensen et al., Biochemistry, 57: 1821-1832 (2018). Enzymatic synthesis is attractive because of its specificity and efficiency and because of its use of mild aqueous reaction conditions which eliminates the need for handling hazardous wastes.

Currently, most enzymatic approaches employ template-free polymerases to repeatedly add 3'-O-blocked nucleoside triphosphates to a single stranded initiator or an elongated strand attached to a support followed by deblocking until a polynucleotide of the desired sequence is obtained, e.g. Jensen et al. (cited above). A variety of 3'-O-blocking groups are available, but of particular interest is the use of the 3'-amino blocking group because of its small size and facile cleavage conditions, e.g. U.S. Pat. Nos. 7,544,794 and 8,212,020. The synthesis of 3'-O-amino-2'deoxyribonucleoside-5'-triphosphates follows the scheme illustrated in FIG. 1 starting from the corresponding 2'-deoxyribonucleoside. After protection of the 5'-hydroxy group, an O-amino moiety is provided in a "masked" (or "protected") form as an N-hydroxyphthalimide moiety, which is inserted at the 3' position, through two subsequent hydroxy inversions under Mitsunobu conditions (Swamy et al., Chem. Rev. 109: 2551-2651 (2009)). Both 3'-O-amino group and 5'-hydroxy group of the nucleoside are then deprotected. However, the triphosphorylation of the 5'-hydroxy group requires that the 3'-O-amino group be protected again, which is accomplished by converting it to an oxime which, in turn, is finally deprotected after the triphosphorylation reaction by treatment with alkoxylamine. Unfortunately, however, this conventional deprotection approach further causes some cleavage of 3'-O-amine. The presence of 3'-hydroxyl-2'-deoxynucleoside triphosphates in the enzymatic coupling reactions in polynucleotide synthesis allows double additions to growing chains to produce difficult-to-remove "n+1" failure sequences in the polynucleotide product.

In view of the above, the enzymatic synthesis of polynucleotides using template-free polymerases would be advanced if methods were available for synthesizing 3'-O-amino-2'-deoxynucleoside triphosphates without the presence of 3'-hydroxyl-2'-deoxynucleoside triphosphate contaminants.

SUMMARY OF THE INVENTION

The invention relates to methods for preparing 3'-O-amino-2'-deoxyribonucleoside-5'-triphosphates with reduced 3'-hydroxy-2'-deoxyribonucleoside-5'-triphosphate contamination. The invention also includes compositions made by methods of the invention.

In some embodiments, such methods of the invention comprise the following steps: (a) protecting 5'-hydroxy group of a 2'-deoxyribonucleoside; (b) converting (S)-3'-hydroxy group of the compound obtained in step (a) into (R)-3'-hydroxy group; (c) reacting the product of step (b) with an N-hydroxyphthalimide to produce a 5'-O-protected-3'-O-phthalimido-2'-deoxynucleoside; (d) deprotecting the 5'-hydroxy group of the product of step (c); (e) converting the product of step (d) to a 3'-O—(N-acetone-oxime)-2'-deoxynucleoside; (f) triphosphorylating 5'-hydroxy group of the product of step (e) to give a 3'-O—(N-acetone-oxime)-2'-deoxynucleoside triphosphate; and (g) converting the product of step (f) to a 3'-O-amine-2'-deoxynucleoside triphosphate by treating the product of step (f) with an aryl-oxyamine.

In some embodiments, such compositions comprise an aqueous solution containing a 3'-O-amino-2'-deoxyribonucleoside-5'-triphosphate and an aryl-oxyamine at a concentration of less than 2% by volume.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

DETAILED DESCRIPTION OF THE INVENTION

Figure 1:
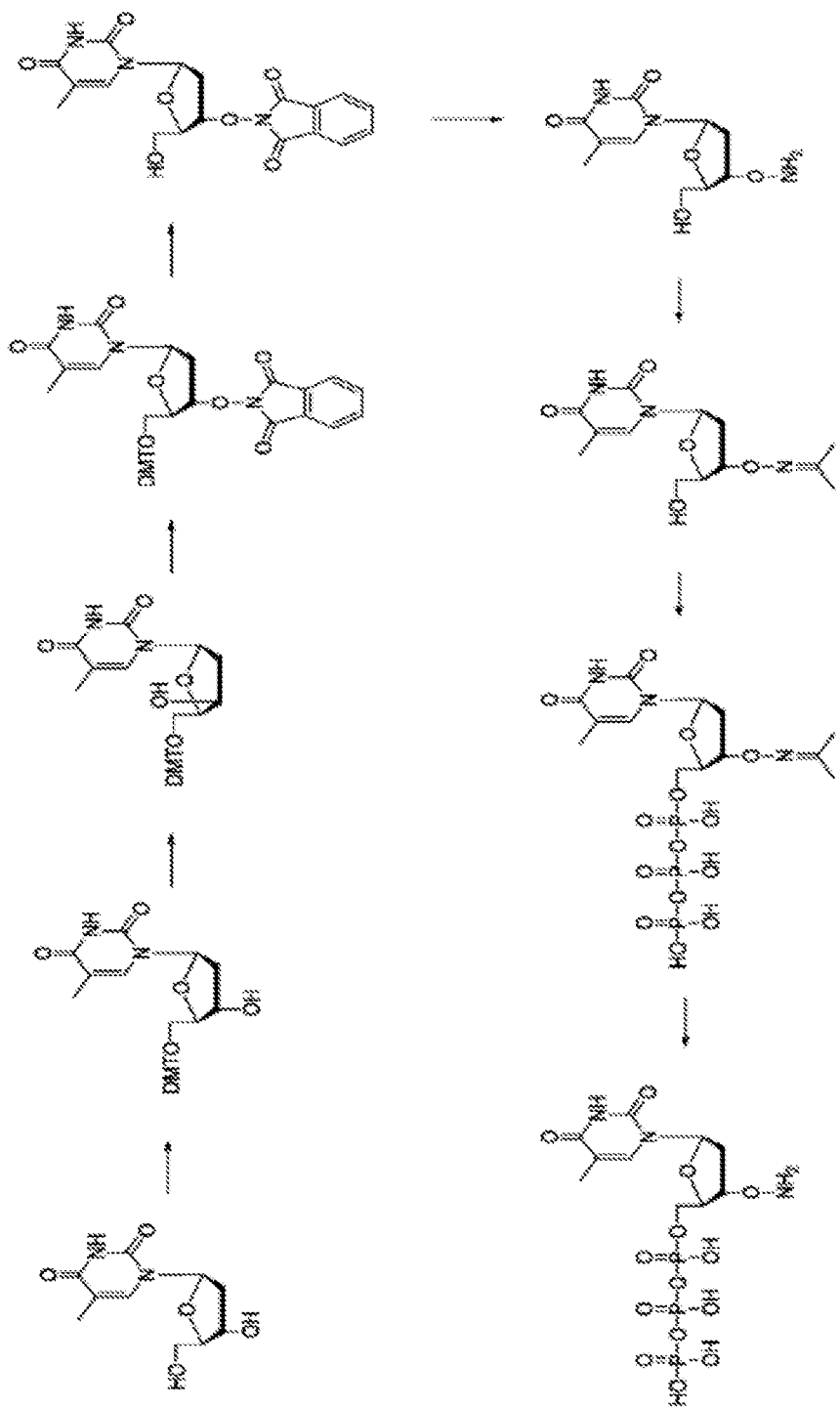
FIG. 1 illustrates the conventional synthesis scheme for making 3'-O-amine-2'-deoxynucleoside triphosphate monomer.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The present invention relates to a method for preparing 3'-O-amino-2'-deoxyribonucleoside-5'-triphosphates using the general steps of:

(a) protecting 5'-hydroxy group of a 2'-deoxyribonucleoside;

(b) converting (S)-3'-hydroxy group of the compound obtained in step (a) into (R)-3'-hydroxy group;

(c) reacting the product of step (b) with an N-hydroxyphthalimide to produce a 5'-O-protected-3'-O-phthalimido-2'-deoxynucleoside;

(d) deprotecting the 5'-hydroxy group of the product of step (c);

(e) converting the product of step (d) to a 3'-O—(N-acetone-oxime)-2'-deoxynucleoside;

(f) triphosphorylating 5'-hydroxy group of the product of step (e) to give a 3'-O—(N-acetone-oxime)-2'-deoxynucleoside triphosphate; and (g) converting the product of step (f) to a 3'-O-amine-2'-deoxynucleoside triphosphate.

The terms "(S)" or "(R)" preceding a group or a moiety, such as in "(R)-3'-hydroxy group", refers to the absolute configuration of the carbon substituted by said group. The position of the carbon may also follow the terms "(S)" or "(R)". In "(R)-3'-hydroxy group", the carbon in position 3' which is substituted with a hydroxy group, has an R absolute configuration.

The 2'-deoxynucleosides of adenine, guanine, cytosine, thymine and uracil, are respectively 2'-deoxyadenosine, 2'-deoxyguanosine, 2'-deoxycytidine, 2'-deoxythymidine and 2'-deoxyuridine.

The above general steps along with numerous specific embodiments are disclosed in the following references: DeClercq et al, European patent application EP0381335; Kondo et al., Symp. Nucleic Acids Chem., 16: 93-96 (1985); Burgess et al., J. Chem. Soc. Chem. Comm., 8: 915-916 (1994); Huffer et al., Nucleosides, Nucleotides & Nucleic Acids, 29(11): 879-895 (2010); Sarac et al., International patent publication WO2020/043846; and U.S. Pat. Nos. 7,544,794; 8,034,923; 8,212,020; and 10,472,383.

Figure 2:
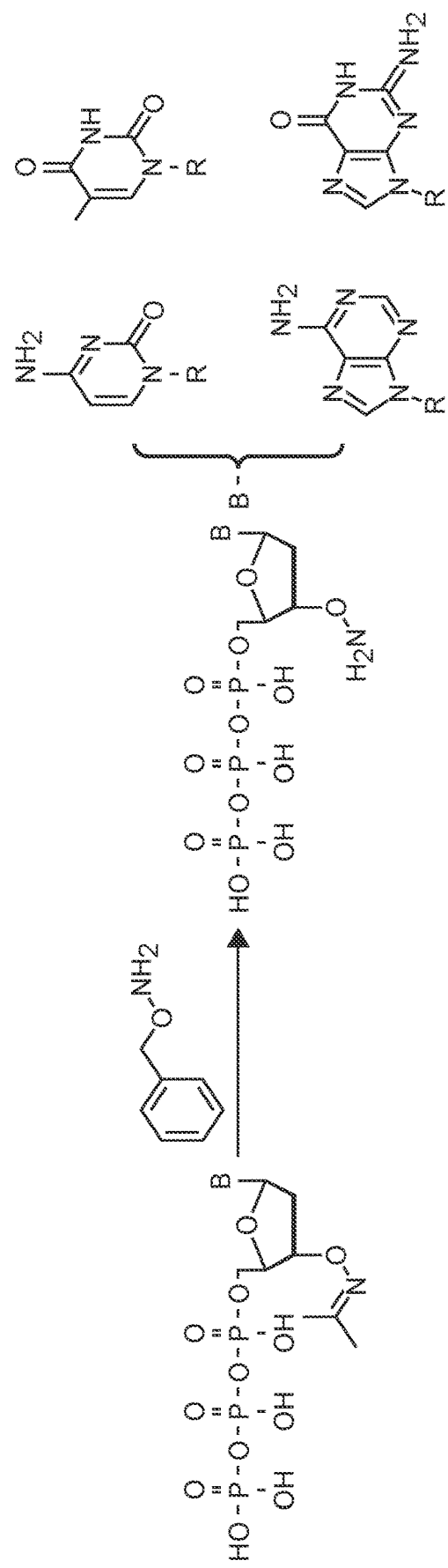
FIG. 2 illustrates an embodiment of the invention for converting, or deprotecting, a 3'-acetone-oxime-nucleoside-triphosphate to a 3'-ONH2-nucleoside triphosphate using benzylhydroxylamine.

In accordance with the invention, the 3'-O—(N-acetone-oxime)-2'-deoxynucleoside triphosphate of step (f) is converted to a 3'-O-amine-2'-deoxynucleoside triphosphate by treating with an aryl-oxyamine, as illustrated in FIG. 2. In some embodiments, the aryl-oxyamine is an unsubstituted or substituted O-benzylhydroxylamine or a substituted or unsubstituted phenylhydroxylamine. Exemplary substituents include methoxy, nitro, halo, wherein in particular halo is fluoro, chloro or bromo. Exemplary substituted O-benzylhydroxylamines include, but are not limited to, O-(2,3,4,5,6-Pentafluorobenzyl)hydroxylamine, and O-(4-Nitrobenzyl)hydroxylamine. In one embodiment, the aryl-oxyamine used with the method of the invention is O-benzylhydroxylamine. In another embodiment, the aryl-oxyamine used with the method of the invention is a substituted or unsubstituted phenylhydroxylamine. As above, exemplary substituents include methoxy, nitro, halo, wherein in particular halo is fluoro, chloro or bromo. The conversion step (g) may be performed using an aqueous solution of an aryl-oxyamine. In some embodiments, pyrimidine 3'-O—(N-acetone-oxime)-2'-deoxynucleoside triphosphates are converted or deprotected to form 3'-O-amine-2'-deoxynucleoside triphosphates at a pH between 6.8 and 7.0. In some embodiments, purine 3'-O—(N-acetone-oxime)-2'-deoxynucleoside triphosphates are converted or deprotected to form 3'-O-amine-2'-deoxynucleoside triphosphates at a pH between 6.0 and 6.8. In some embodiments, for such conversions a concentration of aryl-oxyamine is used which is high enough to bring about the conversion but low enough not to require purification of 3'-O-amine-2'-deoxynucleoside triphosphates prior to use in polynucleotide synthesis. In some embodiment, such concentration of aryl-oxyamine is in the range of from 1 to 100 percent (v/v). In some embodiment, such concentration of aryl-oxyamine is in the range of from 1 to 2 percent (v/v). In other embodiments, such concentration of aryl-oxyamine is less than 2 percent (v/v). In other embodiments, such concentration of aryl-oxyamine is less than 1 percent (v/v).

In some embodiments, aryl-oxyamines used in the method of the invention include substituted or unsubstituted O-benzylhydroxylamine, substituted or unsubstituted O-phenylhydroxylamine, substituted or unsubstituted O-phenylethyldydroxylamine, substituted or unsubstituted O-benzyloxyethylhydroxylamine, and substituted or unsubstituted O-phenoxyethylhyroxylamines, wherein the substituents are selected from halo, methoxy, nitro.

In some embodiments, halo is fluoro, chloro or bromo. In some embodiments, aryl-oxyamines used in the method of the invention include, but are not limited to, O-benzylhydroxylamine, O-phenylhydroxylamine, O-[(2-Methoxyphenyl)methyl]hydroxylamine, O-[(3,5-Dichlorophenyl)methyl]hydroxylamine, O-(3-Chlorobenzyl)hydroxylamine, O-(4-Nitrobenzyl)hydroxylamine, O-(4-Methoxybenzyl)hydroxylamine, O-[(3,4-Dichlorophenyl)methyl]hydroxylamine, O-(2-Chlorobenzyl)hydroxylamine, O-[4-(Trifluoromethyl)benzyl]hydroxylamine, O-[(2,5-Dichlorophenyl)methyl]hydroxylamine, O-(2-Methylbenzyl)hydroxylamine, Pentafluorobenzyl)hydroxylamine, O-(4-Nitrobenzyl)hydroxylamine, O-(2-(Benzyloxy)ethyl)hydroxylamine, O-(4-Bromophenyl)hydroxylamine, O-[2-(Trifluoromethyl)phenyl]hydroxylamine, or O-(2-Phenoxyethyl)hydroxylamine.

Figure 4:
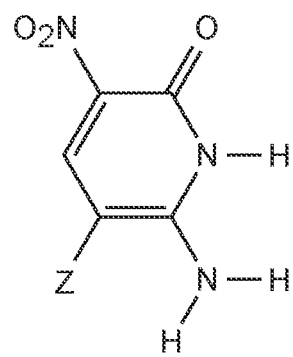
FIG. 4 illustrates examples of bases for 3'-O-amino-2'-deoxyribonucleoside-5'-triphosphate, according to the invention, wherein Z is a 1' carbon of a 2'-deoxyribose-5'-triphosphate, R is either H, $CH_3$, or a linking group, and X is either N or C—R.
Figure 4:
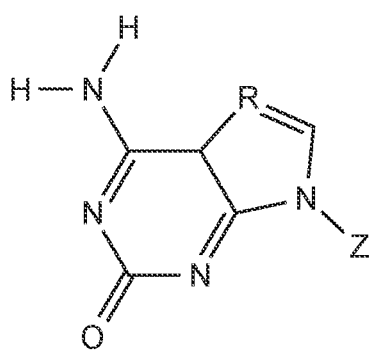
Figure 4:
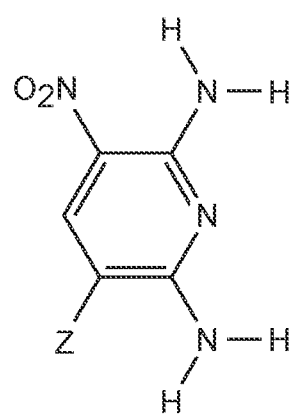
Figure 4:
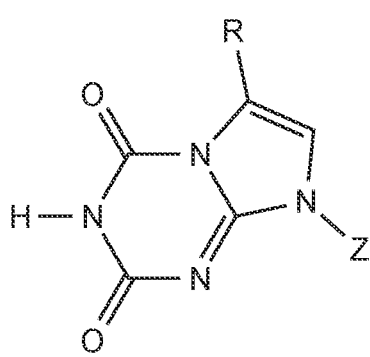
Figure 4:
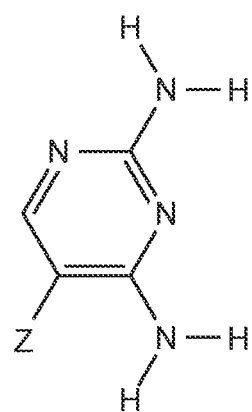
Figure 4:
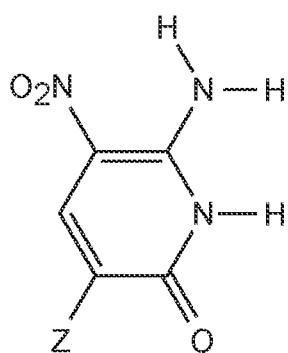
Figure 4:
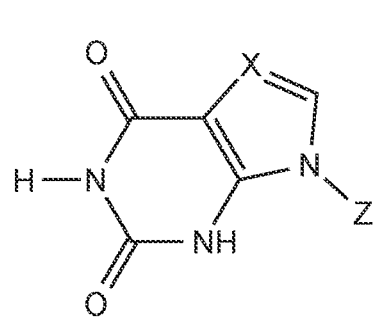
Figure 4:
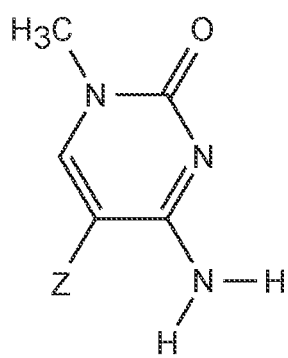
Figure 4:
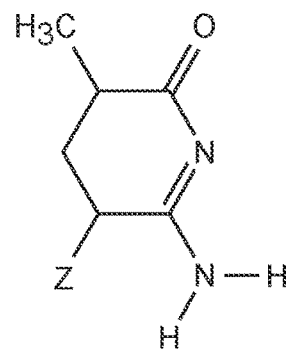
Figure 4:
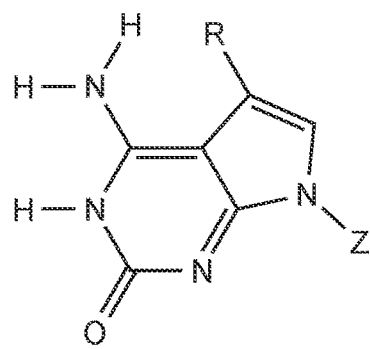
Figure 4:
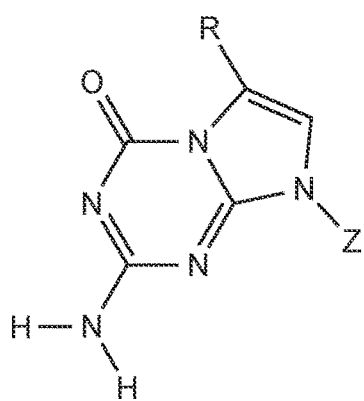
Figure 4:
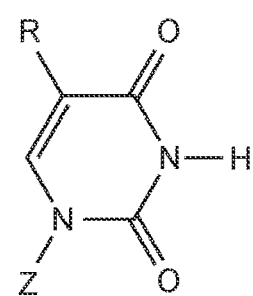
Figure 4:
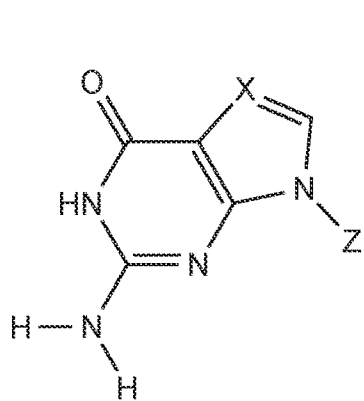
Figure 4:
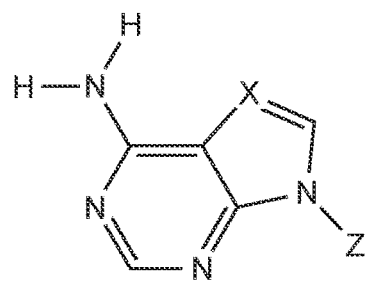
Figure 4:
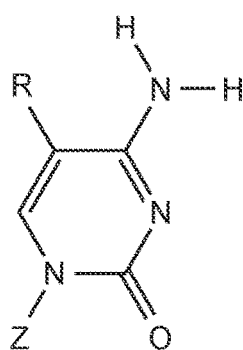
Figure 4:
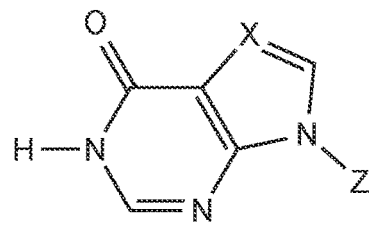

It is also the purpose of the present invention to provide a composition comprising an aqueous solution containing a 3'-O-amino-2'-deoxyribonucleoside-5'-triphosphate and an aryl-oxyamine at a concentration of less than 2% by volume. In a particular embodiment, said aryl-oxyamine is O-benzylhydroxylamine or O-phenylhydroxylamine. Particularly, said 3'-O-amino-2'-deoxyribonucleoside-5'-triphosphate may have a base selected from the group consisting of adenine, thymine, guanine, cytosine, uracil, inosine, xanthine or hypoxanthine. In an embodiment, 3'-O-amino-2'-deoxyribonucleoside-5'-triphosphate has a base selected from the group consisting of base illustrated FIG. 4. Advantageously, the linking group is alkyl linkers, alkenyl linkers, thioether linkers, aminoalkyl, aminoallyl, azidealkyl, azideallyl propargylamine, bis-propargyl, or bis-propargyl-PEG.

Example 1

Deprotection of Purine Nucleobases (A, G)

3'-O-Amino-2'-deoxyguanosine-5'-triphosphate

Figure 3A:
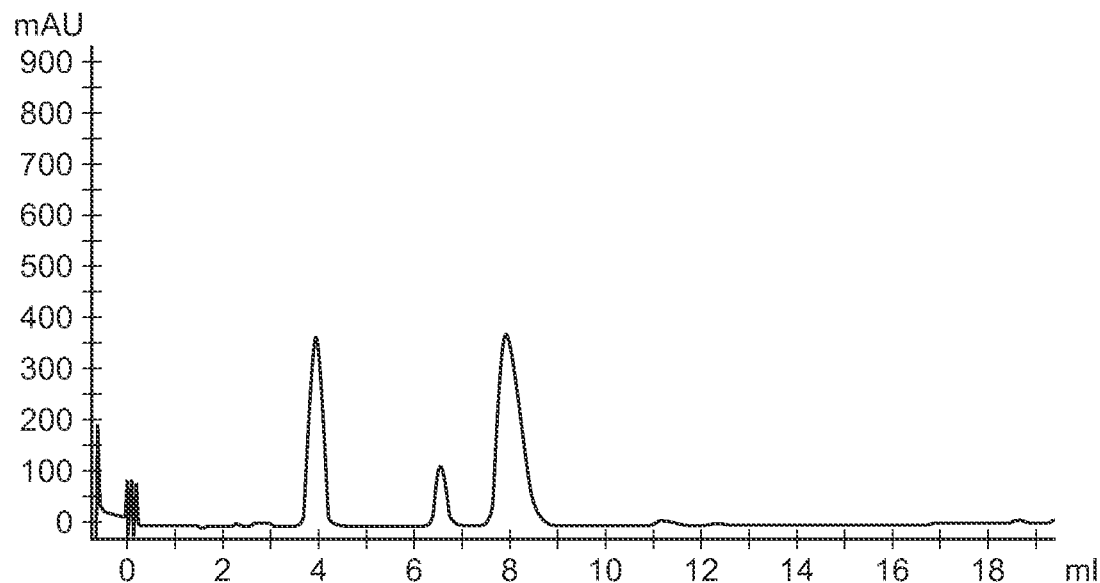
FIG. 3A is a chromatogram of a crude reaction product described in Example 1.
Figure 3B:
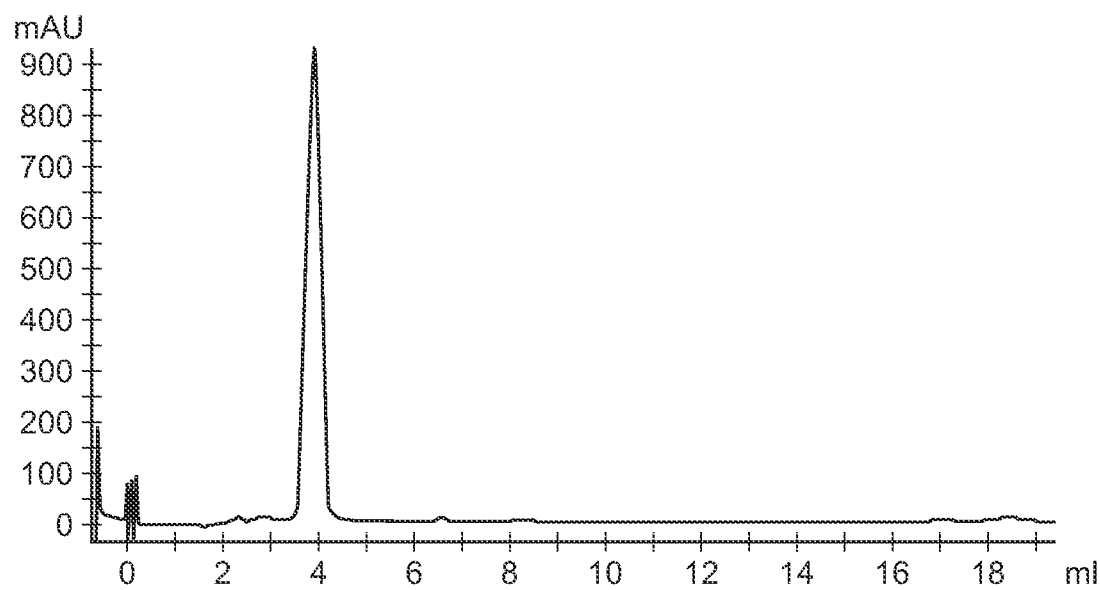
FIG. 3B is a chromatogram of the desired 3'-O-amino-2'-deoxyguanosine-5'-triphosphate product of Example 1.

To a solution of 3'-O—(N-Acetone-oxime)-2'-deoxyguanosine-5'-triphosphate (5.0 mL, 5.0 mmol, 100 mM stock solution) was added water 5.0 mL and O-benzylhydroxylamine (6.2 mL, 50 mmol) the pH was adjusted to 6.5 by adding 10% w/w of aqueous acetic acid. The reaction was stirred for 6 hours. The aqueous phase was extracted with diethyl ether (3×50 mL). The water phase was frozen and freeze dried for 1 hour. FIG. 3A is a chromatogram of the above crude reaction mixture after 2 hours. Excess O-benzylhydroxylamine is removed by liquid-liquid extraction with an organic solvent. The aqueous composition of 3'-ONH2-nucleoside triphosphates may contain a low amount of O-benzylhydroxylamine, sodium acetate and sodium chloride. FIG. 3B is an HPLC chromatogram of the 3'-O-Amino-2'-deoxyguanosine-5'-triphosphate product. The liquid-liquid extraction solvent in the examples is diethyl ether, but can be any organic solvent such as methyl tert-butyl ether, dichloromethane, toluene, pentane etc. and mixtures thereof.

Example 2

Deprotection of Pyrimidine Nucleobases (T, C)

3'-O-Amino-2'-deoxycytidine-5'-triphosphate

To a solution of 3'-O—(N-Acetone-oxime)-2'-deoxycytidine-5'-triphosphate (5.0 mL, 5.0 mmol, 100 mM stock solution) was added water 5.0 mL and O-benzylhydroxylamine (6.2 mL, 50 mmol) the pH was adjusted to 6.8 by adding 10% w/w of aqueous acetic acid. The reaction was stirred for 6 hours. The aqueous phase was extracted with diethyl ether (3×50 mL). The water phase was frozen and freeze dried for 1 hour.

What is claimed is:

1. A method of preparing 3'-O-amino-2'-deoxyribonucleoside-5'-triphosphates comprising the steps of:
   (a) protecting a 5'-hydroxy group of a 2'-deoxyribonucleoside;
   (b) converting an (S)-3'-hydroxy group of the compound obtained in step (a) into an (R)-3'-hydroxy group;
   (c) reacting the product of step (b) with an N-hydroxyphthalimide to produce a 5'-O-protected-3'-O-phthalimido-2'-deoxynucleoside;
   (d) deprotecting the 5'-hydroxy group of the product of step (c);
   (e) converting the product of step (d) to a 3'-O—(N-acetone-oxime)-2'-deoxynucleoside;
   (f) triphosphorylating the 5'-hydroxy group of the product of step (e) to give a 3'-O—(N-acetone-oxime)-2'-deoxynucleotide triphosphate; and
   (g) converting the product of step (f) to a 3'-O-amine-2'-deoxynucleotide triphosphate by treating the product of step (f) with an aryl-oxyamine selected from the group consisting of O-benzylhydroxylamine, O-benzylhydroxylamine substituted with halo or methoxy, substituted or unsubstituted O-benzyloxyethylhydroxylamine, O-benzylhydroxylamine, O-[(2-Methoxyphenyl)methyl]hydroxylamine, O-[(3,5-Dichlorophenyl)methyl]hydroxylamine, O-(3-Chlorobenzyl)hydroxylamine, O-(4-Methoxybenzyl)hydroxylamine, O-[(3,4-Dichlorophenyl)methyl]hydroxylamine, O-(2-Chlorobenzyl)hydroxylamine, O-[4-(Trifluoromethyl)benzyl]hydroxylamine, O-[(2,5-Dichlorophenyl)methyl]hydroxylamine, O-(2-Methylbenzyl)hydroxylamine, O-(2,3,4,5,6-Pentafluorobenzyl)hydroxylamine, O-(2-(Benzyloxy)ethyl)hydroxylamine, O-(4-Bromophenyl)hydroxylamine, O-[2-(Trifluoromethyl)phenyl]hydroxylamine, and O-(2-Phenoxyethyl)hydroxylamine.

2. The method of claim 1, wherein said aryl-oxyamine is O-benzylhydroxylamine.

3. The method of claim 1 wherein the aryloxamine is present during step g) at a concentration of less than 2% by volume.

4. A composition comprising:
   an aqueous solution containing
      a 3'-O-amino-2'-deoxyribonucleotide-5'-triphosphate, and
      an aryl-oxyamine at a concentration of less than 2% by volume.

5. The composition of claim 4, wherein said aryl-oxyamine is O-benzylhydroxylamine or O-phenylhydroxylamine.

6. The composition of claim 4, wherein said 3'-O-amino-2'-deoxyribonucleoside-5'-triphosphate has a base selected from a group consisting of adenine, thymine, guanine, cytosine, uracil, inosine, xanthine and hypoxanthine.

7. The composition of claim 4, wherein said 3'-O-amino-2% deoxyribonucleoside-5'-triphosphate has a base selected from a group consisting of:

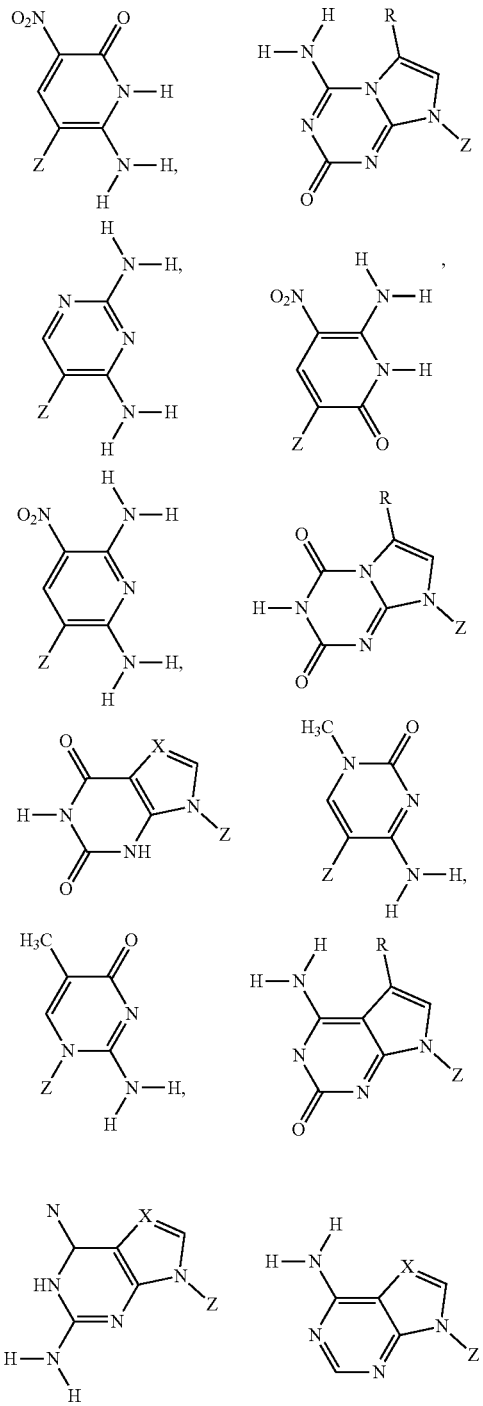

-continued
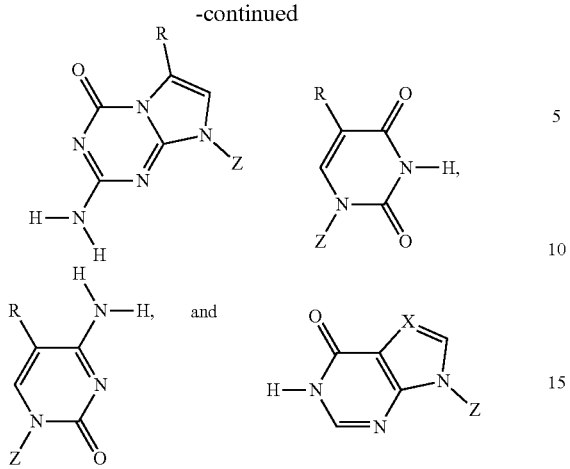
wherein
- Z is a 1' carbon of a 2'-deoxyribose-5'-triphosphate,
- R is H, CH$_3$, or a linking group, and
- X is either N or C—R.
8. The composition of claim 7, wherein said linking group is one of alkyl linkers, alkenyl linkers, thioether linkers, aminoalkyl, aminoallyl, azidealkyl, azideallyl propargylamine, bis-propargyl, or bis-propargyl-PEG.
* * * * *